(12) United States Patent
Tang et al.

(10) Patent No.: US 10,765,352 B2
(45) Date of Patent: Sep. 8, 2020

(54) MULTI-SENSOR NON-INVASIVE BLOOD GLUCOSE MONITORING INSTRUMENT BASED ON IMPEDANCE SPECTROSCOPY-OPTICAL METHOD

(71) Applicants: GLOBAL HEALTH ARK MEDICAL TECHNOLOGY (BEIJING) CO. LTD, Beijing (CN); TSINGHUA UNIVERSITY, Beijing (CN)

(72) Inventors: Fei Tang, Beijing (CN); Zhanxiao Geng, Beijing (CN); Xiaohao Wang, Beijing (CN); Zhiwei Fan, Beijing (CN)

(73) Assignees: Global Health Ark Medical Technology (Beijing) Co. Ltd., Beijing (CN); Tsinghua University, Beijing (CN)

( * ) Notice: Subject to any disclaimer, the term of this patent is extended or adjusted under 35 U.S.C. 154(b) by 221 days.

(21) Appl. No.: 15/744,469

(22) PCT Filed: Oct. 31, 2017

(86) PCT No.: PCT/CN2017/108521
§ 371 (c)(1),
(2) Date: Jan. 12, 2018

(87) PCT Pub. No.: WO2018/090817
PCT Pub. Date: May 24, 2018

(65) Prior Publication Data
US 2019/0261900 A1    Aug. 29, 2019

(30) Foreign Application Priority Data

Nov. 21, 2016  (CN) .......................... 2016 1 1048179

(51) Int. Cl.
*A61B 5/145*    (2006.01)
*A61B 5/1455*   (2006.01)
(Continued)

(52) U.S. Cl.
CPC ............ *A61B 5/1477* (2013.01); *A61B 5/053* (2013.01); *A61B 5/1455* (2013.01);
(Continued)

(58) Field of Classification Search
CPC . A61B 5/1477; A61B 5/14532; A61B 5/1455; A61B 5/6824; A61B 5/053; A61B 5/7203
See application file for complete search history.

(56) References Cited

U.S. PATENT DOCUMENTS

2005/0192488 A1*  9/2005  Bryenton .............  A61B 5/1455
                                                        600/301
2010/0076330 A1   3/2010  Kimura et al.
(Continued)

FOREIGN PATENT DOCUMENTS

CN          1596826 A      3/2005
CN        101390751 A      3/2009
(Continued)

*Primary Examiner* — Eric F Winakur
(74) *Attorney, Agent, or Firm* — Saliwanchik, Lloyd & Eisenschenk

(57) ABSTRACT

A multi-sensor non-invasive blood glucose monitoring instrument based on impedance spectroscopy-optical method, which belongs to a blood glucose measuring instrument for human body. The blood glucose monitoring instrument comprises a detection probe, a microprocessor, a display unit and a storage unit. The detection probe comprises a temperature and humidity sensor, an LED array, a photoelectric sensor, a pair of low-frequency electrodes, and a pair of high-frequency electrodes. The high-frequency electrode employs parallel electrodes, a matching inductor is directly soldered to the positive electrode or negative electrode of the electrode, and a shielding electrode is provided (Continued)

around the high-frequency electrode. The distance between the two low-frequency electrodes is 1 cm-2 m, and the low-frequency electrodes can test the low-frequency impedance of the tissue stably. The temperature and humidity sensor and the tested part of human body form an enclosed space, and slits or pores are arranged in the wall of the enclosed space to form a balanced heat and moisture storage structure. The non-invasive blood glucose monitoring instrument incorporates the impedance spectroscopy method and the optical method, and can obtain more accurate blood glucose levels with improved sensor design.

9 Claims, 2 Drawing Sheets

(51) Int. Cl.
*A61B 5/053* (2006.01)
*A61B 5/1477* (2006.01)
*A61B 5/00* (2006.01)
*G01N 27/02* (2006.01)

(52) U.S. Cl.
CPC ........ *A61B 5/14532* (2013.01); *A61B 5/6802* (2013.01); *A61B 5/6824* (2013.01); *A61B 5/7203* (2013.01); *A61B 5/7225* (2013.01); *G01N 27/026* (2013.01); *A61B 2562/0209* (2013.01); *A61B 2562/029* (2013.01); *A61B 2562/0238* (2013.01); *A61B 2562/0271* (2013.01)

(56) References Cited

U.S. PATENT DOCUMENTS

| | | |
|---|---|---|
| 2010/0179403 A1 | 7/2010 | Martinsen et al. |
| 2013/0211204 A1 | 8/2013 | Caduff et al. |

FOREIGN PATENT DOCUMENTS

| | | |
|---|---|---|
| CN | 102293654 A | 12/2011 |
| CN | 103815916 A | 5/2014 |
| CN | 106691449 A | 5/2017 |
| CN | 206491802 U | 9/2017 |
| WO | 9939627 A1 | 8/1999 |

* cited by examiner

MULTI-SENSOR NON-INVASIVE BLOOD GLUCOSE MONITORING INSTRUMENT BASED ON IMPEDANCE SPECTROSCOPY-OPTICAL METHOD

CROSS REFERENCE TO RELATED APPLICATIONS

This application is a National Stage Application of International Application Number PCT/CN2017/108521, filed Oct. 31, 2017; which claims priority to Chinese Application No. 201611048179.3, filed Nov. 21, 2016.

TECHNICAL FIELD

The present invention relates to non-invasive blood glucose monitoring of human body, particularly to a multi-sensor non-invasive blood glucose monitoring instrument based on impedance spectroscopy-optical method, and belongs to the technical field of medical instruments.

BACKGROUND ART

Diabetes is a group of metabolic diseases characterized by high blood glucose, and at present there is no radical cure to it yet. The treatment of diabetes needs frequently monitoring glucose to control the blood glucose level. The conventional invasive blood sampling method has obvious defects, and, it causes wound and pain to the patient during measurement, and is inconvenient for continuous monitoring. Non-invasive blood glucose monitoring technology overcomes the drawbacks of the conventional method, which can effectively meet the demand of diabetic patients for real-time and frequent monitoring of blood glucose concentration. Non-invasive method is the developing direction of blood glucose detection technology. Optical method is the most studied non-invasive glucose monitoring method. However, due to numerous interferences and individual differences, most of the them are still in a laboratory research stage.

Since Lukaski put forward using bioelectrical impedance analysis (BIA) to measure body components of human in 1985, researchers have used BIA method to differentiate components of human body, including fats, muscles, minerals, and aqueous substances, etc. Fatty substances and non-fatty substances have different current conducting properties, so that different tissues and organs have different impedance characteristics. The Inbody series human body composition analyzers developed by a Korean listed company measure the balance condition of human body components at high accuracy. It employs a multi-frequency bioelectrical impedance analysis method in different segment of body.

Based on the biological impedance technique, some progress has been made in the research on non-invasive blood glucose monitoring based on impedance spectroscopy (IS) method. Most of researches on impedance spectroscopy focus on frequencies within 0-50 kHz and below 10 MHz. Harry Richardson Elden, et al., (WO1999039627 A1) from USA measures impedance amplitude and phase of the skin of human body at specific frequency points (20 kHz, 500 kHz) and utilizes a linear combination of impedance and phase to predict blood glucose; a research team led by Kiseok Song in Korea incorporates impedance spectroscopy and infrared spectrometry to carry out non-invasive blood glucose tests, with a frequency range of 10 kHz-76 kHz. Researches at a low frequency are relatively easy since there is no need to concern the impact of radio frequency transmission, high-frequency noise interference, and electrode polarization, etc.; however, at low frequency, the current bypasses cells and flows through the extracellular fluid, influencing the result of non-invasive blood glucose monitoring.

A research team led by Caduff A (US2013/0211204A1, U.S. Pat. No. 7,693,561B2) in Swiss has found that there is an apparent relation between blood glucose concentration and impedance value in higher frequency bands. The research team designed an impedance measurement system within 30-60 MHz frequency, and studied the correlation between obtained impedance information and blood glucose. The high-frequency method has a high requirement for stability of tissue characteristics. However, owing to a severe difference in skin thickness and tissues among different individuals, it is hard to attain a satisfactory result if the high-frequency method is used alone. In the subsequent researches, the research team began to employ a multi-sensor and multi-parameter measurement method to improve the accuracy, including electrodes in high frequency band, intermediate frequency band and low frequency band, temperature, humidity and optical sensors. The electrodes included a vertical bar electrode and annular electrodes around the vertical bar electrode, and the distances between the vertical bar electrode and the surrounding annular electrodes were 0.3 mm, 1.5 mm, and 4 mm respectively; the wavelengths used by the optical sensor were 550/660/880 nm. The electrodes used by the research team had a strip shape at one end and an annular shape at the other end, and the electrodes operating at different frequencies were close to each other and were surrounded by identical grounding wires; therefore, interference existed among the electrodes; since two electrodes operating at the same frequency were very close to each other, the penetration depth in the tissue was shallow; the temperature and humidity sensors were directly attached to the skin, causing humidity saturation easily and influencing temperature and humidity test.

Contents of the Invention

The object of the present invention is to overcome the drawbacks in the prior art, and the present invention provides a multi-sensor non-invasive blood glucose monitoring instrument based on impedance spectroscopy-optical method, in order to further improve blood glucose measuring accuracy.

The technical scheme of the present invention is as follows:

A multi-sensor non-invasive blood glucose monitoring instrument based on an impedance spectroscopy-optical method, comprising a detection probe, a microprocessor, a display unit, and a storage unit. The detection probe comprises a pair of high-frequency electrodes, a pair of low-frequency electrodes, a temperature and humidity sensor, an LED array, a photoelectric sensor, and a contact plate. The microprocessor controls an excitation signal generation circuit to generate high frequency and low frequency excitation signals. Feedback signals from the high-frequency electrodes and the low-frequency electrodes are inputted via an amplitude and phase detection circuit to the microprocessor, and high-frequency impedance and low-frequency impedance are obtained through calculation. Temperature signals and humidity signals, which are measured with the temperature and humidity sensor, are conditioned and inputted to the microprocessor. The LED array is controlled by a transmitter control circuit. Light intensity signals, which are measured by the photoelectric sensor, are amplified and filtered and then inputted to the microprocessor to obtain optical characteristics of the tissue. The microprocessor inputs the processing result to the display system for display, and the test data is saved in the storage unit at the same time. The monitoring instrument is characterized in that: the high-frequency electrodes employ parallel electrodes, and a matching inductor L is directly soldered to the positive electrode or negative electrode; the distance between the positive electrode and the negative electrode of the low-frequency electrodes is 1 cm~2 m; the vertical distance from the bottom of the temperature and humidity sensor to the bottom of the contact plate is 0.1 mm~20 mm; the temperature and humidity sensor and the tested part of human body form an enclosed space, and slits or pores are arranged in the wall of the enclosed space to form a balanced heat and moisture storage structure.

The above-mentioned technical scheme is further characterized in that: a shielding electrode is provided around the high-frequency electrodes, the shielding electrode is connected to the positive electrode or negative electrode of the high-frequency electrodes via the inductor L. The high-frequency electrodes preferably are flexible electrodes.

Another technical feature of the present invention is: the enclosed space formed by the temperature and humidity sensor and the tested part of human body is formed by a sensor mounting plate and a base plate with a cavity structure, and the base plate is mounted right above the contact plate.

The multi-sensor non-invasive blood glucose monitoring instrument based on an impedance spectroscopy-optical method in the present invention is also characterized in that: the LED array 4 and the photoelectric sensor 5 are arranged in the blood flow direction of the human body, and the center distance between them is 1 mm-200 mm.

The LED array 4 in the present invention contains 4 LEDs, the wavelengths of which are 660 nm, 760 nm, 850 nm and 940 nm respectively.

The detection probe in the present invention is fixed to the tested part of human body via a wrist strap. The contact plate is a rubber plate.

Compared with the Prior Art, the Present Invention has the Following Advantages and Prominent Effects:

(1) in the present invention, the distances between the high-frequency electrodes for impedance spectroscopy are optimized, a matching inductor is directly soldered to one of the high-frequency electrodes, a conducting rectangular frame arranged around the electrodes is directly connected to one of the electrodes, the electrodes are flexible and can be attached to the skin closely, so that noise interference is reduced; (2) since the distance between the low-frequency electrodes for impedance spectroscopy in the present invention is far, the measured signals are more stable, and the correlation of the extracted characteristic parameters with the blood glucose is higher; (3) a temperature and humidity sensor is utilized in the present invention to measure the temperature and humidity of skin surface, so as to correct the measurement result obtained in the impedance spectroscopy and photoelectrical channels; the temperature and humidity sensor is kept at a certain distance from the skin of human body, and forms a non-enclosed space with slits or pores; thus, a balanced heat and moisture storage structure is formed, to eliminate the influence of body temperature change and sweatiness on the measurement, thus the obtained temperature and humidity result is more accurate.

In the figures: 1—low-frequency electrodes; 2—temperature and humidity sensor; 3—high-frequency electrodes; 4—LED array; 5—photoelectric sensor; 6—contact plate; 7—base plate; 8—top cover; 9—temperature and humidity sensor mounting plate; 10—shielding electrode; 11—pores in the temperature and humidity sensor mounting plate; L—matching inductor of high-frequency electrodes

EMBODIMENTS

The structure, working principle and working process of the multi-sensor non-invasive blood glucose monitoring instrument based on an impedance spectroscopy-optical method will be further detailed with reference to the attached drawings.

Figure 1:
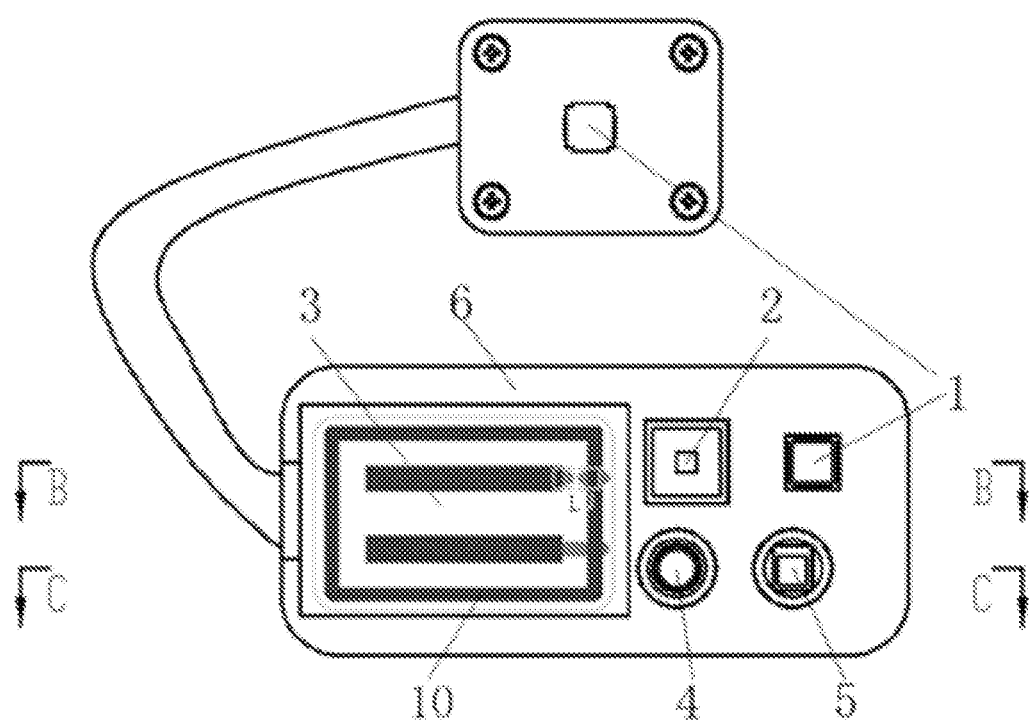
FIG. 1 is a top view of the probe viewed from the direction of the base plate in the present invention.
Figure 2:
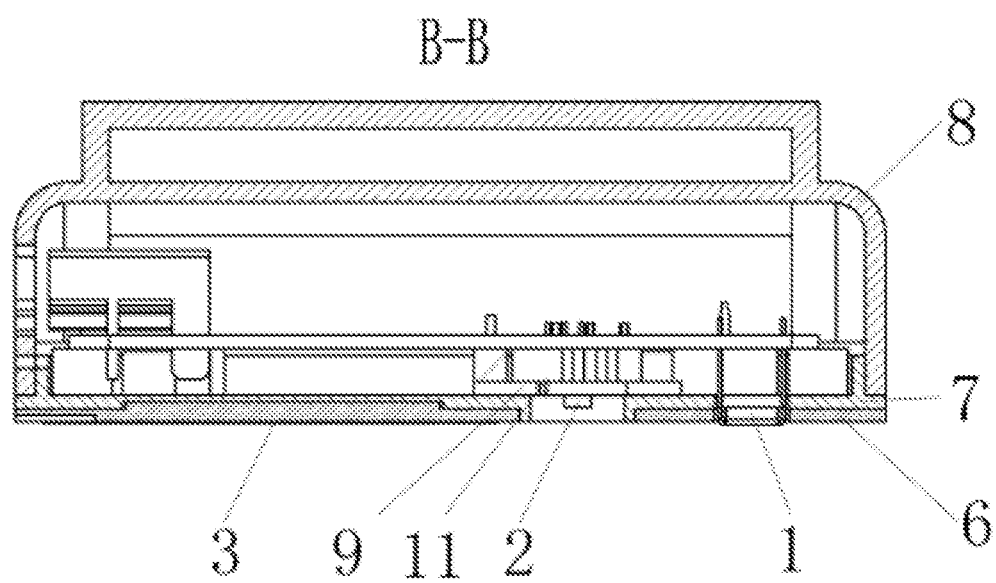
FIG. 2 is a sectional view B-B of the structure in FIG. 1.
Figure 3:
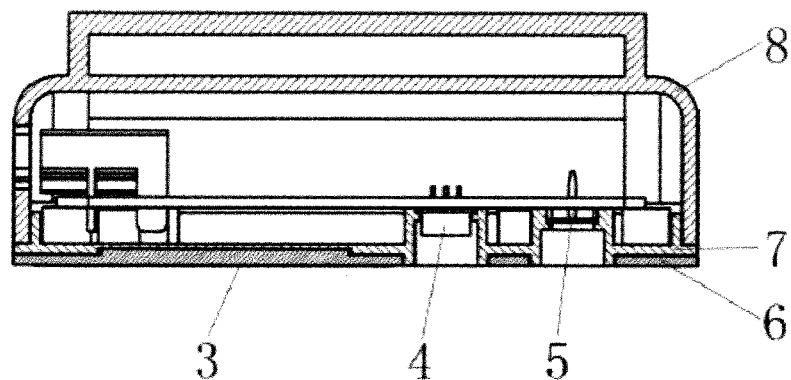
FIG. 3 is a sectional view C-C of the structure in FIG. 1.

FIGS. 1, 2 and 3 are schematic structural diagrams of the detection probe of the multi-sensor non-invasive blood glucose monitoring instrument based on an impedance spectroscopy-optical method. The detection probe comprises a temperature and humidity sensor 2, an LED array 4, a photoelectric sensor 5, a pair of low-frequency electrodes 1, a pair of high-frequency electrodes 3, and a contact plate 6. In order to ease the use of the instrument and make the structure more compact, the detection probe in the present invention may further comprises a housing, which comprises a base plate 7 and a top cover 8; a structure on the top cover 8 is used to fix the housing to a tested part (e.g., wrist or upper arm, etc.) of human body via a wrist strap, and the wrist strap may be made of an elastic material and provided with a hook & loop fastener; in order to improve the comfort level during use of the instrument, the contact plate 6 is made of rubber material.

According to the requirement for measurement, the high-frequency electrodes 3 in the present invention employs parallel electrodes, a matching inductor L is directly soldered to the positive electrode or negative electrode of the high-frequency electrodes, and a shielding electrode 10 is provided around the high-frequency electrodes, and the shielding electrode is connected to the positive electrode or negative electrode of the high-frequency electrodes via the inductor L. In order to improve the quality of contact between the high-frequency electrodes and the body skin, the high-frequency electrodes may be flexible electrodes. There is a certain distance (1 cm~2 m) between the two low-frequency electrodes 1. The low-frequency electrodes may adopt a split design, wherein, one of the low-frequency electrodes is arranged separately, and the other one is arranged together with the rest sensors, as shown in FIG. 1. The low-frequency electrodes 1, temperature and humidity sensor 2, LED array 4, photoelectric sensor 5, and high-frequency electrodes 3 in the present invention are arranged on the base plate 7, and aligned along the tested part of human body. The base plate 7 and the top cover 8 in the present invention may be made of an insulating material (e.g., PVC material).

The high-frequency excitation electrical signals frequency range is 1 MHz~100 MHz, the low-frequency electrodes are made of stainless steel or any other metal material, such as CuCrZr, BeCu, $CuAl_2O_3$, Ag/AgCl, and the excitation electrical signals frequency range is 1 KHz~1 MHz.

The vertical distance from the bottom of the temperature and humidity sensor 2 to the bottom of the contact plate 6 is 0.1 mm~20 mm; the temperature and humidity sensor 2 and the tested part of human body form an enclosed space, and slits or pores are arranged in the wall of the enclosed space to form a balanced heat and moisture storage structure. The enclosed space formed by the temperature and humidity sensor 2 and the tested part of human body is formed by a sensor mounting plate 9 and a base plate 7 with a cavity structure, and the base plate 7 is mounted right above the contact plate 6. The slits or pores in the wall of the enclosed space may be pores arranged in the temperature and humidity sensor mounting plate, as indicated by 11 in FIG. 2.

The LED array 4 in the present invention contains 4 LEDs, the wavelengths of which are 660 nm, 760 nm, 850 nm and 940 nm respectively. The LED array 4 and the photoelectric sensor 5 are arranged in the blood flow direction in the human body, and the center distance between them is 1 mm-200 mm.

Figure 4:
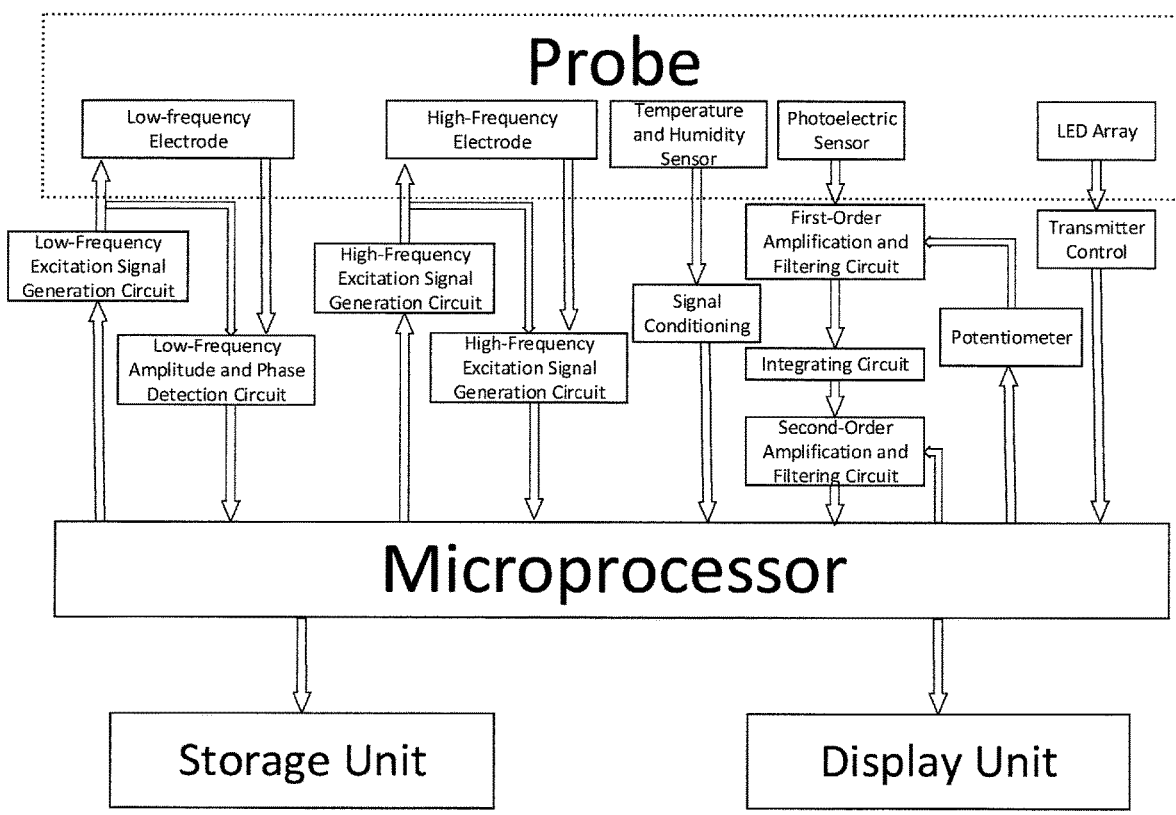
FIG. 4 is a functional block diagram of the circuits of the non-invasive blood glucose detection instrument.

FIG. 4 is a functional block diagram of the circuits of the data processing and display system in the present invention. The data processing and display system comprises a microprocessor, a display unit and a storage unit connected to the microprocessor respectively; the high-frequency electrodes 3 contact with the tested part (e.g., wrist or upper arm, etc.) and transfers a high-frequency excitation swept-frequency signal generated by a high-frequency excitation signal generation circuit into the human body, a high-frequency amplitude and phase detection circuit receives the high-frequency excitation signal and a feedback signal from the tested part of human body, processes the signals, and then transmit the amplitude ratio and phase difference between the two signals to the microprocessor, so that a high-frequency impedance spectroscopy $Z_H$ is obtained finally; the low-frequency electrodes 1 contact with the tested part (e.g., wrist or upper arm, etc.), and transfers a low-frequency excitation swept-frequency signal generated by a low-frequency excitation signal generation circuit into the human body, a low-frequency amplitude and phase detection circuit receives the low-frequency excitation signal and a feedback signal from the tested part of human body, processes the signals, and then transmits the amplitude ratio and phase difference between the two signals to the microprocessor, so that a low-frequency impedance spectroscopy $Z_L$ is obtained finally; a reflected light intensity signal A measured by the photoelectric sensor 5 passes through a first-order amplification and filtering circuit, an integrating circuit, and a second-order amplification and filtering circuit, and then is inputted to the microprocessor by means of analog acquisition; the LED array 4 is controlled by a transmitter control circuit, and the microprocessor is connected with the transmitter control circuit through control lines; the microprocessor is connected with the first-order amplification and filtering circuit through control lines and a potentiometer switching circuit, and is connected with the second-order amplification and filtering circuit through control lines.

The measuring principle of the multi-sensor non-invasive blood glucose monitoring instrument based on impedance spectroscopy-optical method is as follows: in the present invention, blood glucose measurement is carried out on the basis of high-frequency impedance spectroscopy principle, low-frequency impedance spectroscopy principle, and optical principle respectively, and then the blood glucose levels obtained on the basis of the three principles are considered comprehensively, to obtain an optimal merged result of blood glucose level.

In the measuring principle based on impedance spectroscopy, it is believed that the electrolytic equilibrium between the tissue fluid and the cells is upset in the glucose metabolism process, and thereby the electrolyte concentrations inside and outside the cells are changed, and the permeability characteristic of the cell membranes is changed, resulting in change of the dielectric constant, and on a macro level resulting in change of impedance information. Based on the impedance model of human body, in a low-frequency excitation state (<100 kHz), the current can't pass through the cell membranes, and the information obtained is mainly information on the tissue fluid; meanwhile, since there is no need to concern the impact of radio frequency transmission, high-frequency noise interference, and electrode polarization, etc., the information on the composition of the tissue fluid can be obtained more easily, and the fluctuations of blood glucose concentration in the tissue fluid in the metabolic process can be characterized at a macro level. In the present invention, the low-frequency impedance measurement is right based on that principle. The obtained information on fluctuations of blood glucose is characterized by extracting characteristic values from the low-frequency impedance spectroscopy $Z_L$ and processing with certain algorithm. Under high-frequency excitation (>10 MHz), the current penetrates through the cell membranes; thus, complete information on the tissue fluid and the cell sap can be obtained, and the variations of blood glucose concentration can be characterized more sensitively and more quickly; however, the high-frequency information is susceptible to the influence of skin thickness and the tissue difference, and other fluctuating factors in the tissue fluid, has poor anti-interference ability, and is difficult to characterize the blood glucose level separately. In the present invention, characteristic values are extracted from the high-frequency impedance spectroscopy $Z_H$ and are processed with certain algorithm to characterize the blood glucose. In the present invention, the information of low-frequency impedance spectroscopy and high-frequency impedance spectroscopy are used in combination to realize merged processing, so as to obtain a result superior to the separate measurements.

Based on the optical measurement principle, it is believed that when the light waves of a particular wavelength penetrate through the tissues of human body, a part of energy of the light waves will be absorbed by human body, and the difference in the absorption characteristics reflects the magnitude of blood glucose concentration in the human body; by measuring the intensity of reflected light, the corresponding blood glucose level can be obtained; the transmitted light intensity is measured by the photoelectric sensor 5.

The working process of the multi-sensor non-invasive blood glucose monitoring instrument based on impedance spectroscopy-optical method is as follows:

The detection probe described in the present invention is fixed to the tested part (e.g., wrist or upper arm, etc.) of human body via a wrist trap, the detection probe operates with multiple channels in a cyclic manner, and the temperature and humidity sensor 2, high-frequency electrodes 3, low-frequency electrodes 1, and photoelectric sensor 5 acquire the data in corresponding channels respectively and transmits the acquired data in four channels to the data processing and display system.

The temperature and humidity sensor measures the temperature signal T at the tested part of human body and the ambient humidity signal H, and the signals passes through transmission line and signal conditioning circuits sequentially and are transmitted to the microprocessor.

The high-frequency electrodes 3 contact with the tested part (e.g., wrist or upper arm, etc.) and transfers a high-frequency excitation swept-frequency signal generated by a high-frequency excitation signal generation circuit into the human body, the high-frequency amplitude and phase detection circuit receives the high-frequency excitation signal and a feedback signal from the tested part of human body, processes the signals, and then transmit the amplitude ratio and phase difference between the two signals to the microprocessor, so that the high-frequency impedance spectroscopy $Z_H$ is obtained finally.

The low-frequency electrodes 1 contact with the tested part (e.g., wrist or upper arm, etc.), and transfers a low-frequency excitation swept-frequency signal generated by a low-frequency excitation signal generation circuit into the human body, the low-frequency amplitude and phase detection circuit receives the low-frequency excitation signal and a feedback signal from the tested part of human body, processes the signals, and then transmits the amplitude ratio and phase difference between the two signals to the microprocessor, so that the low-frequency impedance spectroscopy $Z_L$ is obtained finally.

The light waves emitted from the LED array 4 passes through the tested part (e.g., finger or ear, etc.) and then reflection spectrum signals $A_1 \sim A_4$ are generated and received by the photoelectric sensor 5, then the signals are processed through the first-order amplification and filtering circuit, the integrating circuit, and the second-order amplification and filtering circuit, and transmitted to the microprocessor. The operation of the LED array 4 is controlled by a transmitter control circuit, which is connected to the microprocessor through control lines; the first-order amplification and filtering circuit is controlled by a potentiometer switching circuit, which is connected to the microprocessor through control lines; the second-order amplification and filtering circuit is directly connected to the microprocessor through control lines. Thus, the transmitter control circuit, the first-order amplification and filtering circuit, and the second-order amplification and filtering circuit are subjected to the control of the microprocessor.

Under the control of the microprocessor, all signals are transmitted to the microprocessor, and those signals are processed under the non-invasive blood glucose detection principle described in the present invention, so that the blood glucose level measured by the instrument is obtained. The blood glucose level and key intermediate data are inputted through transmission lines to the display unit and the storage unit respectively, to realize data display and storage functions. As the core unit for data processing, the microprocessor has the following three functions: the first function is to acquire all data and carry out data computation and processing; the second function is to generate control signals to control the transmitter control circuit, the second-order amplification and filtering circuit, and the potentiometer switching circuit; the third function is to transmit the data to the display unit and storage unit, to accomplish display and storage respectively.

The invention claimed is:

1. A multi-sensor non-invasive blood glucose monitoring instrument based on impedance spectroscopy optics, the monitoring instrument comprising:
   a detection probe;
   a microprocessor;
   a display unit; and
   a storage unit,
   wherein the detection probe comprises a pair of high-frequency electrodes, a pair of low-frequency electrodes, a temperature and humidity sensor, an LED array, a photoelectric sensor, and a contact plate,
   wherein the microprocessor controls an excitation signal generation circuit to generate high frequency and low frequency excitation signals,
   wherein feedback signals from the high-frequency electrodes and the low-frequency electrodes are inputted to the microprocessor via an amplitude and phase detection circuit, and then high-frequency impedance and low-frequency impedance are obtained through calculation,
   wherein temperature signals and humidity signals of a tested part are measured with the temperature and humidity sensor, and then are conditioned and inputted to the microprocessor,
   wherein the LED array is controlled by a transmitter control circuit,
   wherein light intensity signals measured by the photoelectric sensor are amplified and filtered, and then inputted to the microprocessor to obtain optical characteristics of tissue of the tested part,
   wherein the microprocessor is configured to use a model to calculate a blood glucose concentration of the test part based on the optical characteristics, the high-frequency impedance and low-frequency impedance, and the conditioned temperature signals and humidity signals,
   wherein the microprocessor outputs the calculated blood glucose concentration to the display unit for display, and the optical characteristics, the high-frequency impedance and low-frequency impedance, and the conditioned temperature signals and humidity signals are saved in the storage unit at the same time,
   wherein the high-frequency electrodes comprise a pair of parallel electrodes, and a matching inductor L is directly soldered to one of the electrodes,
   wherein a distance between a positive electrode and a negative electrode of the low-frequency electrodes is 1 cm-2 m,
   wherein a vertical distance from a bottom of the temperature and humidity sensor to a bottom of the contact plate is 0.1 mm-20 mm, and
   wherein the temperature and humidity sensor and the tested part form an enclosed space, and slits or pores are arranged in a wall of the enclosed space to form a balanced heat and moisture storage structure.

2. The monitoring instrument according to claim 1, wherein a shielding electrode is provided around the high-frequency electrodes, and the shielding electrode is connected to a positive electrode or a negative electrode of the high-frequency electrodes via the matching inductor L.

3. The monitoring instrument according to claim 1, wherein the low-frequency electrodes adopt a split design.

4. The monitoring instrument according to claim 1, wherein, wherein the high-frequency electrodes are flexible electrodes.

5. The monitoring instrument according to claim 1, wherein the enclosed space between the temperature and humidity sensor and the tested part is formed by a sensor mounting plate and a base plate with a cavity structure, and wherein the base plate is mounted on top of the contact plate.

6. The monitoring instrument according to claim 1, wherein a center distance between the LED array and the photoelectric sensor is 1 mm-200 mm.

7. The monitoring instrument according to claim 1, wherein the LED array comprises 4 LEDs, the wavelengths of which are 660 nm, 760 nm, 850 nm and 940 nm, respectively.

8. The monitoring instrument according to claim 1, wherein the detection probe is fixed to the tested part via a wrist strap.

9. The monitoring instrument according to claim 1, wherein the contact plate is a rubber plate.

* * * * *